(12) United States Patent
Qiu et al.

(10) Patent No.: US 7,078,575 B1
(45) Date of Patent: Jul. 18, 2006

(54) PROCESSES FOR PREPARING HIGH PURITY POLYCYCLIC FLUOROALKANES

(75) Inventors: Weiming Qiu, Wilmington, DE (US); Sheng Peng, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/149,614

(22) Filed: Jun. 9, 2005

(51) Int. Cl.
*C07C 19/08* (2006.01)
(52) U.S. Cl. ..................................................... 570/130
(58) Field of Classification Search ................. 570/130
See application file for complete search history.

(56) References Cited

U.S. PATENT DOCUMENTS 4,647,581 A    3/1987    Kolhl et al.

FOREIGN PATENT DOCUMENTS

JP           2005035941 A  *  7/2003
JP           2005 035941       2/2005

OTHER PUBLICATIONS

McBee et al., Diels-Alder Reactions with Fluorine Containing Olefins, J. Amer. Chem. Soc., 1954, pp. 915-917. vol. 77.
J. March, Mechanisms and Structure, Advanced Organic Chemistry, 4$^{th}$ Edition, 1992, p. 598, 766 and 771.
Switkes et. al., Immersion Lithography at 157 nm, J. Vac. Sci. Technol. B, Nov./Dec. 2001, pp. 2353-2356, vol. 19 (6).
M. Switkes et. al., Resolution Enhancement of 157 nm Lithography by Liquid Immersion, Proc. SPIE, 2002, pp. 459-465, vol. 4691.

* cited by examiner

*Primary Examiner*—Johann Richter
*Assistant Examiner*—Kellette Gale

(57) ABSTRACT

Processes for preparing high purity polycyclic fluoroalkanes are provided. The polycyclic fluoroalkanes are useful as solvents, cleaning agents, heat transfer fluids, refrigerants, lubricants, and, in a preferred embodiment, by virtue of high refractive index and high transparency to UV wavelengths, optical applications in the vacuum ultraviolet (VUV).

13 Claims, No Drawings

PROCESSES FOR PREPARING HIGH PURITY POLYCYCLIC FLUOROALKANES

FIELD OF THE INVENTION

The present invention is directed to processes for preparing high purity polycyclic fluoroalkanes useful as solvents, cleaning agents, heat transfer fluids, refrigerants, lubricants, and, in preferred embodiments, by virtue of unusually high refractive index and high transparency to UV wavelengths, optical applications in the vacuum ultraviolet (VUV).

BACKGROUND OF THE INVENTION

McBee et al. J. Amer. Chem Soc. 77 pp 915–917 (1954) teaches Diels Alder addition of a fluorinated olefin to a cyclic diene to form less than 10% of a compound having the formula

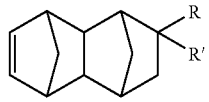

where R=H, $CF_3$, or $C_2F_5$; and R'=H or $CH_3$.

Koebl et al., U.S. Pat. No. 4,647,581 discloses 2-trifluoromethyl-2,3,3-trifluoro-1,2,3,4,5,8,9,10-octahydro-1,4:5,8-dimethanonaphthalene.

Catalytic hydrogenation of a double bond to a saturated Structure is well known in the literature. (March J., *Advanced Organic Chemistry*, 4$^{th}$ Ed., 1992, p 771 and references therein).

Takashi et al., JP2005035941A, discloses the Pd/C—catalyzed hydrogenation of the double bond in

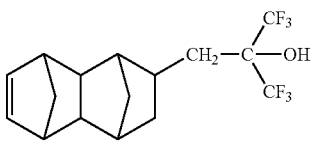

by bubbling room temperature hydrogen through the refluxing starting material for five hours at atmospheric pressure.

It is known in the art that olefins contacted with an acid, such as sulfuric acid, nitric acid or perchloric acid, form species with higher boiling point and/or higher water solubility (March J., *Advanced Organic Chemistry*, 4$^{th}$ Ed., 1992, p 766 and references therein). It is also known in the art that SO3 reacts with a number of highly absorbing compounds, such as aromatics, ketones, aldehydes, carboxylic acid, and olefins, to form species with higher bp and/or higher water solubility (March J., *ibid*, p 598 and references therein).

Immersion photolithography is described in Switkes et al, *J. Vac. Sci. Technol. B*, 19 (6), 2353 6, November/December 2001; and, M. Switkes et al, "Resolution enhancement of 157-nm photolithography at 157 nm exposure wavelength by liquid immersion", *Proc. SPIE* Vol. 4691, pp. 459465 (2002). In immersion photolithography the optical source, the target surface, or the entire lithographic apparatus is immersed in a highly transparent high refractive index liquid. Realization of the potential benefits of this technology is dependent upon identifying liquids with exceptionally high transparency in the VUV/DUV and photochemical stability. The present invention is directed to these and other important ends.

SUMMARY OF THE INVENTION

The present invention provides a process comprising combining in a pressure vessel an olefin represented by the Structure I

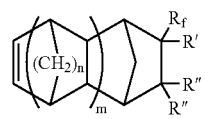

wherein $R_f$ is a fluorinated alkyl of 1–10 carbons that is linear, branched, or cyclic; R' is H, F, an alkyl of 1–6 carbons that is linear, branched, or cyclic, or a fluorinated alkyl of 1–6 carbons that is linear, branched, or cyclic;
  each R" is independently H or F, n=0 or 1, and m=1 or 2 provided that m is not 2 when n=0; and a hydrogenation catalyst;
  sealing the vessel;
  removing water vapor and air;
  pressurizing the vessel with hydrogen to a pressure in the range of 10 to 1000 psig;
  heating the vessel to a temperature from room temperature to 200° C.;
  allowing the resulting reaction to proceed for a period of time of 1 to 8 hours to form a reaction product;
  contacting said reaction product with sulfuric acid or oleum to form an acid treated reaction product; and, contacting said acid treated reaction product with silica gel.

DETAILED DESCRIPTION

The products of the processes of the present invention are polycyclic fluoroalkanes useful as solvents, cleaning agents, lubricants, and optical transmission media.

The polycyclic fluoroalkanes can be represented by the formula II where m, n, $R_f$, R', and R" are defined above.

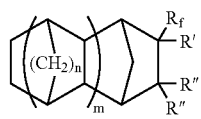

In a preferred embodiment, n=1, m=1, $R_f$ is perfluoromethyl or perfluoroethyl, and R' is H or F. Most preferably $R_f$ is perfluoromethyl. In a preferred embodiment, the molar ratio of fluorine to hydrogen in the product II, F/H is less than 0.5, but greater than zero.

One of skill in the art will appreciate that several possible stereoisomers are possible for olefins of Structure I and the products of Structure II. Such stereoisomers are intended to be within the scope of the present invention.

The polycyclic fluoroalkanes show surprisingly high suitability for use in applications requiring transparency in the vacuum ultraviolet (VUV) such as optical adhesive compositions, solvents for pellicle polymers, index matching fluids and the like. Of particular note is the suitability thereof in the emerging field of immersion photolithography in the VUV, particularly at 193 nm. In immersion photolithography, a process used for the fabrication of microcircuits as described in Switkes et al., *op. cit.*, a target surface is partially or wholly immersed, preferably wholly immersed, in a medium of high transparency and higher refractive index than air or other gaseous atmospheres.

Unless otherwise stated, concentrations expressed herein as parts per million (ppm) refer to parts per million by weight on the basis of the total weight of the composition referred to.

When an amount, concentration, or other value or parameter is recited herein as either a range, preferred range or a list of upper values and lower values, the recited amount, concentration, or other value or parameter is intended to include all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In preferred embodiments, the polycyclic fluoroalkanes have an F/H ratio of 0.5 or lower, but greater than zero, a refractive index of at least 1.50 and an absorbance at 193 nm of 2.0 cm$^{-1}$ or lower.

The inventors have found surprisingly that a balance of desirable properties for VUV immersion photolithography applications is achieved by employing polycyclic fluoroalkanes having an F/H ratio of less than 0.5—that is, by employing saturated polycyclic hydrocarbons in which on a mole-% basis, only about one third or fewer of the hydrogens are replaced by fluorines.

The transparency and photochemical stability of the polycyclic fluoroalkanes render the polycyclic fluoroalkanes particularly suitable for use in immersion photolithography in the vacuum ultraviolet/deep ultraviolet (VUV/DUV) region of the electromagnetic spectrum. However, it is highly desirable that the highest achievable standards of purity be maintained throughout the preparation, purification, and handling of the polycyclic fluoroalkanes, because advanced optical applications such as immersion lithography in the VUV are extremely intolerant of contaminants. Olefins are sources of photochemical instability, and increase absorbance tremendously. Oxygen is a source of photochemical instability, and long-term storage problems deriving therefrom.

Catalytic hydrogenation of olefins is well known. Takashi et al. *op. cit.*, for example, teach a catalytic hydrogenation process which can readily be applied to an olefin of Structure I to prepare the polycyclic fluoroalkane of Structure II. However, modern optical applications in the VUV wavelength region, in particular, immersion photolithography, impose extraordinarily high standards of purity on any organic chemical considered for use therein. Conventional methods may not produce polycyclic fluoroalkanes having an absorbance of 2 cm$^{-1}$ or less and adequate photochemical stability at the high-energy wavelengths of the VUV.

The inventors have found that polycyclic fluoroalkanes having desirable properties for VUV applications can be produced by the processes of the present invention. While it is not intended that the present invention be bound by any particular theory, the processes of the present invention are designed to drive the catalytic hydrogenation reaction to as close as possible to complete conversion by employing elevated pressures and temperatures, leaving less than about 0.5% residue of unconverted olefin, and then employing further purification steps to scavenge the remaining olefin and remove other trace organic impurities. Further purification steps include contacting with sulfuric acid and contacting with silica gel.

One embodiment of the present invention is a process comprising combining in a pressure vessel an olefin represented by the Structure I

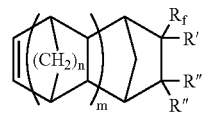

I wherein $R_f$ is a fluorinated alkyl of 1–10 carbons that is linear, branched, or cyclic; R' is H, F, an alkyl of 1–6 carbons that is linear, branched, or cyclic or a fluorinated alkyl of 1–6 carbons that is linear, branched, or cyclic;

each R" is independently H or F, n=0 or 1, and m=1 or 2 provided that m is not 2 when n=0; and a hydrogenation catalyst;

sealing the vessel;

removing water vapor and air;

pressurizing the vessel with hydrogen to a pressure in the range of 10 to 1000 psig;

heating the vessel to a temperature from room temperature to 200° C.;

allowing the resulting reaction to proceed for 1 to 8 hours to form a reaction product;

contacting said reaction product with sulfuric acid or oleum to form an acid treated reaction product; and, contacting said acid treated reaction product with silica gel.

Preferably n=1, m=1, $R_f$ is perfluoromethyl, R' is F, and each R" is F.

Various additional practical steps can be carried out, as dictated by the specific application. These steps may include extraction of the heterogeneous catalyst, extraction of the silica gel, and extraction of any solvent, if solvent is employed. These are all procedures well known to those skilled in the art. Solids such as catalyst and silica gel can be extracted by ordinary filtration methods. Any solvent can be extracted by distillation.

In the practice of the present invention it is found that catalyst concentrations of 0.15–0.2 mole-% are effective, although concentrations in the range of 0.05–1 mole-% are satisfactory. Larger quantities of catalyst may also be effective, but could complicate extraction thereof. Suitable catalysts include but are not limited to palladium on carbon, Raney nickel, Raney cobalt, platinum metal or its oxide, rhodium, ruthenium and zinc oxide.

The reaction can be carried out using the neat liquid olefin, but it is preferred to form a solution having a concentration above 2 volume percent more preferably from 30 to 80 volume percent. Preferred solvents include methanol, ethanol, THF, acetic acid, acetone, and ethyl acetate.

According to the present invention, upon combination of an olefin of Structure I, a catalyst, and, in preferred embodiments, the solvent, the pressure vessel is sealed. Air and water are removed using known methods. The sealed vessel is then pressurized with hydrogen to at least 10 psig, preferably about 50 psig. Reaction is initiated immediately upon exposure of the olefin to the hydrogen and catalyst. In a preferred embodiment, during the course of reaction, the hydrogen pressure is increased to a pressure as high as 1000 psig, or higher, preferably about 600 psig. In a further preferred embodiment, during the course of the reaction, the temperature of the reaction mixture is raised to a temperature up to 200° C., preferably about 150° C. Increases in pressure and temperature may be continuous or step-wise.

In a typical embodiment of a process of the invention, initial pressurization is to about. 50 psig at room temperature. The reaction is permitted to run until the rate of uptake of $H_2$ begins to decrease—typically within 20–30 minutes. Pressure is then raised to about. 200 psig of hydrogen. After typically about 15 minutes at 200 psig at room temperature, the reaction temperature is increased to 150° C., then the hydrogen pressure is increased to 600 psig. The reaction is continued under these conditions (150° C. and 600 psig pressure hydrogen) for about 2 hours.

In a preferred embodiment, the olefin is combined with methanol in approximately a 50/50 volume percent ratio. At the termination of the reaction, the resulting liquid is filtered to remove the catalyst. The filtrate is mixed with water and forms two layers. The organic layer is isolated, diluted with a solvent such as methylene chloride, washed with more water and then dried. The dried, washed filtrate is then distilled. The distillate is then contacted with typically about. 10 volume percent of concentrated sulfuric acid or oleum (containing up to 15% $SO_3$) followed by a series of aqueous washes to remove the acid. Any means of causing the sulfuric acid or oleum to come into contact with the polycyclic fluoroalkane will suffice to remove olefinic contamination. However, it is preferred that the mixture be stirred for about. 24 hours.

Following contacting with sulfuric acid, and washing, the acid treated polycyclic fluoroalkane product is contacted with silica gel, preferably a thermally activated silica gel, as described herein below. The role of the silica gel is to remove trace organic impurities.

If the degree of conversion achieved in the hydrogenation step is sufficiently high, the sulfuric acid step may be omitted. However, in general, it is preferable to include the hydrogenation step.

The olefinic precursor, II, can be prepared by the well-known Diels-Alder reaction between a fluorinated olefin with a cyclic diene. The reaction can advantageously be performed at a temperature of about 200° C. for about. 48 hours, according to the methods described in McBee et al. *J. Amer. Chem Soc.* 77 pp 915–917 (1954).

While it is not intended to limit the invention, it is estimated that about. 99% conversion may occur in the first twenty to thirty minute stage of reaction at room temperature under less than 50 psig hydrogen pressure. The subsequent elevation of hydrogen pressure and temperature and prolonged reaction time are employed to push the reaction to as close to complete conversion of the olefin as possible.

In order to maximize the utility of the polycyclic fluoroalkanes in optical applications in the VUV, particularly in immersion photolithography, the thus prepared polycyclic fluoroalkane is treated to ensure that oxygen concentration does not exceed 2 parts per million by weight (ppm), and treated to remove trace organic contaminants. The so-treated polycyclic fluoroalkane exhibits absorbance of 2.0/cm$^{-1}$ or lower, preferably 0.1 to 1 cm$^{-1}$, at 193 nm. In a most preferred embodiment of the present invention, the oxygen concentration of the polycyclic fluoroalkane characterized after treatment does not exceed 1 ppm.

Certain organic impurities, such as olefins, substituted cycloalkanes, branched alkanes, oxidation products such as peroxides and ketones, and the like may be present. Some organic impurities are orders of magnitude more absorbing than other organic impurities. So, for example, a suitable polycyclic fluoroalkane contaminated by a percent or two of cyclobutane, which is quite transparent though of high vapor pressure and low refractive index, may be suitable for use in the processes disclosed herein. On the other hand, it may be desirable that the concentration of more highly absorbing contaminants, such as olefins and carbonyls, is on the order of 1 ppm or even less.

Highly absorbing contaminants can be removed from the polycyclic fluoroalkanes by such methods as fractional distillation, sparging, freeze-thaw cycling, zone refining, and treatment with adsorbents such as silica, molecular sieves of various pore sizes, carbon, silica gel, alumina, and mixtures or combinations thereof.

Preferably, the polycyclic fluoroalkane exhibits absorbance of 0.1 to 1 cm$^{-1}$ at 193 nm. One of skill in the art will appreciate the absorbance is preferably as low as possible, provided the oxygen concentration is desirably low. It will be appreciated by one of skill in the art that at purity levels required to achieve this result, the most sensitive measurement of contamination is the spectroscopic absorption itself. In other words the best way to tell that the most important impurities have been removed is to measure the absorbance. Absorbance below 1 cm$^{-1}$ is by far the most sensitive available indicator of purity in regard to trace amounts of absorbers.

The term "absorbance" refers to two related phenomena. On the one hand, the term "absorbance" refers to the actual absorbance of the polycyclic fluoroalkane in actual use in the processes disclosed herein, which can be affected by external influences such as the solubility of a photoresist, as discussed hereinabove. On the other hand, "absorbance" also refers to the analytical spectroscopic method employed to determine absorbance under laboratory conditions. The latter is a highly desirable method for evaluating the concentration of contaminating adsorbents in compositions of high purity.

It has been found that silica gel is a highly effective adsorbent for very small amounts of organic contamination present in the polycyclic fluoroalkanes. Large improvements in transparency have been observed when a polycyclic fluoroalkane has been treated with silica gel.

It may be desirable to first subject the as-prepared polycyclic fluoroalkane to fractional distillation in the cleanest possible, grease-free distillation apparatus. The heart cut of the distillate thus produced is then mixed in the liquid state with concentrated sulfuric acid or oleum followed by separation from concentrated sulfuric acid or oleum, neutralization, washing with water and distillation. This distillate thus produced is then mixed in the liquid state with a mixture of adsorbents, which may include, for example, silica gel, 3A, and 5A zeolite molecular sieves, alumina, or activated carbon. All subsequent handling of the thus purified polycyclic fluoroalkane is then performed in an oxygen-minimized atmosphere, preferably an inert gas atmosphere, most preferably a helium or nitrogen atmosphere. This includes the use thereof in immersion photolithography, which is preferably performed in an oxygen-minimized atmosphere.

Concentrated sulfuric acid or oleum treatment is used before adsorbent treatment. The amounts of concentrated sulfuric acid or oleum for such treatment is dependent on the impurity level in the fluids to be treated. In most cases 2 to 30 volume-% of concentrated sulfuric acid or oleum in volume is found to be effective. It is preferred to use 5 to 15 volume-% concentrated sulfuric acid or oleum. Before treatment with adsorbents, specifically silica gel, the concentrated sulfuric acid or oleum is removed by layer separation, neutralization, and washing with water.

Silica gel and zeolite adsorbents are most effective if activated, preferably by heating while purging with a dry gas flow. It is preferable that adsorbent activation be done immediately prior to use. Activation can be achieved by heating to about 200 to 500° C. under a flow of dry, pure air, nitrogen, or helium for several hours. Air at 500° C. has the advantage of burning most residual organic contaminants off an adsorbent such as a silica gel or a zeolite. The gas flow can be continued as the system cools down to a temperature in the range of room temperature to 100° C. In an alternative procedure the gas flow is stopped and the system sealed off. In another alternative procedure, the gas flow is stopped and the system evacuated as the adsorbent cools to a temperature in the range of room temperature to 100° C. The advantage of stopping the gas flow while the adsorbent is at 500° C. is that this minimizes recontamination from any adventitious impurities in the gas as the adsorbent cools down.

A preferred method of activating the silica gel and zeolite adsorbents is the following. A Hastelloy® tube in a clamshell furnace is loaded with adsorbent and then heated under an air flow for two hours at 500° C. The airflow is stopped and the Hastelloy tube immediately sealed at both ends. Once the sealed Hastelloy® tube has cooled to room temperature, it is transferred to a $N_2$ glove bag where the tube is opened and the adsorbent added to a bottle containing the polycyclic fluoroalkane that is to be purified. Although the ratio of adsorbent to liquid can be varied without limit, it has been found satisfactory to employ one volume of adsorbent for every 1 to 20 volumes of liquid. The actual amount of adsorbent required will depend upon the level of contamination in the as-received liquid. It is therefore desirable to employ some excess to insure maximum effectiveness in removal of contaminants.

A key aspect of any distillation process employed in the purification of the polycyclic fluoroalkanes is that it be performed in the cleanest, least contaminated distillation apparatus possible. It is particularly desirable to exclude oxygen and any adventitious or systemic organic contaminants. It is found in the practice of the invention that employment of grease, including fluorinated greases, such as are commonly employed in distillation and vacuum systems to provide improved sealing and easier part removal can contaminate the distillate herein sufficiently to actually degrade the absorbance. It is therefore highly preferably to perform the distillation in a "grease-free" distillation system. "Grease-free", as used herein, means that no grease is employed when assembling the cleaned parts of the system. One of skill in the art will appreciate that the term "grease-free" does not mean that the invention is not operable should there be some small amount of grease contamination somewhere in the system. To the extent that the system can be cleaned of all grease contamination, the absorbance is advantageously reduced, but "grease-free" is not intended to require the complete absence of any grease in no matter how small a concentration.

There are numerous uses for the highly transparent polycyclic fluoroalkane in the VUV. Contemplated applications include, but are not limited to, optical couplants, optical cements, optical elements such as liquid lenses, index-matching optical inspection media for semiconductor wafers and devices, and immersion fluids, especially for 193 and 248 nm photolithography.

Preferably, the polycyclic fluoroalkane has an F/H ratio of 0.5 or lower, but greater than zero, and has a refractive index within the range of 1.5 to 1.7, more preferably 1.6 to 1.7.

Sparging is a suitable method for removing contaminants from the polycyclic fluoroalkanes, particularly for the removal of oxygen. One method for sparging that can be used is as follows. A glove box is supplied with dry, low-oxygen-content nitrogen such as 99.998% or better nitrogen sold as a cylinder gas by Matheson or by the boil-off of liquid nitrogen. A liquid aliquot of about 10 ml is placed in a 20 ml glass scintillation vial. The sample is transferred into the nitrogen purged dry box. The vial is secured flat on the work surface, the plastic cap is removed from the vial, a disposable glass pipette lowered into the solvent and then nitrogen delivered via the pipette from the same dry, low-oxygen source as the glove box. Flow rate is adjusted to maintain vigorous bubbling of solvent short of causing the solvent to splash out of the vial. Vigorous sparging is continued for 30–60 seconds, long enough to significantly decrease oxygen content and possibly water content without major loss of the polycyclic fluoroalkane to evaporation.

Because available instrumentation has a sensitivity limit of about 1 ppm of oxygen the actual oxygen concentration in a specimen may be considerably lower than 1 ppm. Henry's Law can be employed to estimate the oxygen concentration, using Henry's Law constants available in the literature. Based upon such estimates, it is estimated that the actual oxygen concentration in the polycyclic fluoroalkane when handled in an oxygen-minimized atmosphere is less than 100 ppb (parts per billion).

The nitrogen atmosphere in which the specimens were handled in the specific embodiments herein below described was produced from boiled off liquid nitrogen and is estimated to have had an oxygen concentration of 3–5 ppm.

An alternative method for purifying the polycyclic fluoroalkane for use in the instant process is bulb-to-bulb distillation through a bed of 3 A molecular sieves. For example, two flasks are connected by a tube containing 3 A molecular sieves preheated as described above. One of the flasks is then partially filled with the liquid that is to be purified and the system resealed. The liquid is subjected to three freeze/thaw cycles to remove dissolved oxygen. The system is then thoroughly evacuated after refreezing the liquid with liquid nitrogen. The system is sealed under vacuum and the liquid nitrogen cooling bath transferred from the flask containing the liquid to the empty flask. As the liquid warms towards room temperature it distills through the bed of 3A molecular sieves to the chilled flask. Once distillation is complete the vacuum is relieved with oxygen free nitrogen, the purified liquid allowed to warm to room temperature, and the flask then valved off for subsequent use.

From the stand point of practical utility, it is highly desirable to remove contaminating species that exhibit photochemical reactivity. Such species not only tend to be strongly absorbing in the wavelength region from 170 to 260 nm, but also can undergo photo-induced reactions, often resulting in bubble formation and darkening. Extraction of any one photochemically active species is beneficial whether or not any other photochemically active species present is extracted.

The polycyclic fluoroalkanes can be employed in any number of ways in addition to as an immersion liquid in photolithography. Examples of other applications include those in which the polycyclic fluoroalkane is disposed between a VUV light source and a target. The polycyclic fluoroalkane can be employed neat, as in liquid lenses, index matching fluid, and the like, or it can be an ingredient of a mixture or a diluent such as a solvent for polymers in spin-coating operations, a plasticizer in a polymeric film, or a solvent in an adhesive formulation. In another embodiment, the suitable polycyclic fluoroalkane can be used in optical inspection of patterned or unpatterned objects such as semiconductor wafers, where small size defects of varying optical properties are to be detected. The use of the polycyclic fluoroalkanes as immersion fluids for immersion inspection enables both higher resolution imaging in the inspection, and also reduces optical scattering from the topography of the sample, permitting the inspection of, for example, deep holes that may have defects, such as particulate debris present. In still further embodiments, the polycyclic fluoroalkanes are useful in the fabrication of sheets, layers, coatings, and films used in lenses, light guides, antireflective coatings and layers, windows, protective coatings, and glues suitable for use in VUV photolithography.

The polycyclic fluoroalkanes can also be used in elements in a compound lens designed to reduce chromatic aberrations. Heretofore, only CaF2 and possibly hydroxyl free silica have been viewed as having sufficient transparency at 193 nm to be used in transmissive focusing elements. It is also known, as disclosed in, for example, R. Kingslake, Academic Press, Inc., 1978, Lens Design Fundamentals, p. 77, that by using a second material of different refractive index and dispersion, an achromatic lens can be created.

The present invention is further described but not limited to the following examples.

EXAMPLES

Optical Absorbance Measurements

The transmission based absorbance measurements were made using a Harrick Scientific Corp. (Harrick Scientific Corporation 88 Broadway Ossining, N.Y.) Demountable Liquid Cell model DLC-M13. The cell had an 8 mm aperture, which included (2) 13 mm diameter×2 mm thick $CaF_2$ windows, Viton® polymer o-ring seals, (2) Luer-Lok® fittings for loading sample, assorted Teflon® tetrafluoroethylene (TFE (spacer thicknesses from 6 um to 4000 um. The DLC-M13 was mounted in a variable angle spectroscopic ellipsometer manufactured by J. A. Woollam Co., Inc., Lincoln, Nebr., either a VUV-Vase® model VU-302 for measurements from the near IR to 145 nm, or a DUV-Vase® model V- for measurements from the near IR to 187 nm. The liquid specimen to be tested was held in a cell formed between parallel $CaF_2$ windows by insertion of a Teflon® TFE ring between the windows. Teflon® TFE rings of 6, 25, 100, 500, 920, 2200, 3000, 4000, 6000, and 10000 micrometer thicknesses were used, providing multiple optical path lengths through different aliquots of the same sample. While charging the cell, care was taken to avoid bubbles in the 8 mm diameter window aperture.

The optical absorbance, $A$ ($cm^{-1}$), is defined for purposes herein as the base 10 logarithm of the ratio of the transmission of the $CaF_2$ windows at the test wavelength divided by the transmission at that wavelength of the test sample (windows plus experimental specimen) divided by the thickness (t) of the test specimen To eliminate the effect of multiple reflections in the case of the liquid samples employed herein, absorbance was determined using the relative change in the transmission of multiple liquid filled Harrick cells with differing cell spacer thicknesses. As many as 5 different optical path lengths were employed for a single determination of absorbance.

Harrick Cell Cleaning and Assembly Procedure:

Prior to use, and after each sample run, the Harrick cell was flushed with Vertrel® XF as a cleaning solvent (Miller-Stephenson Chemical Co., Danbury, Conn.). A clean 1 ml Glass syringe (Becton Dickinson, Franklin Lakes N.J.) with a female Luer-Lock fitting was filled with Vertrel® XF and then attached to the male Luer-Lock fitting on the Harrick cell, at which point the Vertrel® XF was flushed through the cell. The cell was then blown dry using "house nitrogen" (produced from the boil off of liquid nitrogen and which has fewer than 3 ppm of water and 5 ppm of oxygen). The cell was then disassembled in reverse order. The $CaF_2$ windows and the selected thickness Teflon® TFE spacers were placed into a 20 ml vial containing Vertrel® XF, the vials were capped and then put into an ultrasonic bath for, 30–60 seconds. The $CaF_2$ windows and spacers were removed form the cleaning vial, given a final rub with cotton swab moistened with Vertrel® XF then dried with air from a puffer bulb. The cell was then reassembled. The cleaning and assembly was done in air.

Loading the Harrick Cell in Air (Lab Hood)

To the thus prepared cell, approximately 0.5 ml of the sample liquid was transferred from its container using a clean 1 ml BD glass syringe, the syringe was then attached into the cell and the cell was filled until the liquid meniscus was visible above the top Luer-Lok® fitting, so that no trapped bubbles were permitted to reside in the cell aperture. Then the top Luer-Lok® fitting on the Harrick cell was capped with the Teflon® TFE plug, and the cell was inverted with the syringe still attached. The syringe was twisted off and the thus exposed cell fitting was capped with another Teflon® TFE plug.

Loading the Harrick Cell in Nitrogen . . . (Nitrogen Dry Box)

A cleaned and assembled cell was placed into either the N2 purged antechamber of a Series 100 Plexiglass Glove Box (Terra Unversal, Anaheim ABOUT) or a previously nitrogen-flushed mini chamber attached to a nitrogen purged Nexus model 100043 Dry Box (Vacuum Atmospheres Co., Hawthorne, Calif.). The antechamber was continually purged with house nitrogen until the oxygen meter on the dry box read 10 ppm $O_2$—approximately 30 minutes. The mini chamber was evacuated then filled with nitrogen three times prior to transfer of the equipment to the dry box.

The manner of specimen introduction into the Harrick Cell was as described in the previous section.

Loading a Dried Sample Into the Harrick Cell in Nitrogen (Nitrogen Dry Box)

A cleaned, assembled cell, with Teflon® TFE plugs (separate; not inserted), a clean 1 ml BD syringe and the selected sample that had been dried over adsorbents still in the sample bottle, were placed in the dry box described above in the manner described.

The sample bottle was opened and the liquid poured into a clean 15 ml BD syringe with a 0.45 micrometer PTFE Luer-Lok® filter. Using the syringe, the liquid was transferred through the filter into a clean, dry 20 ml vial. Approximately 0.5 ml of the thus filtered sample was transferred into the cell as described above.

Absorbance Determination

For the purpose of the examples herein below, the absorbance of a material was determined using the relative transmission methods described above, for various cell thicknesses. The thickness of the test specimen was adjusted so that absorbance of at least 0.1% was achieved in order to keep measurement error the same across multiple specimens.

Absorbance was also measured directly using a Varian Cary 5 UV/Vis/NIR spectrometer. While single measurements in the Varian Cary 5 were not as accurate as relative transmission measurements using multiple path length measurements in a VUV-Vase ellipsometer, data acquisition was much less time-consuming.

Index of Refraction Measurements

The index of refraction of the material and its temperature coefficient was determined using the minimum deviation prism method as described in Sinnock et al. *Phys. Rev.*, 181 (3), p. 1297ff (1969) using the VUV-vase and the DUV-vase instrument (see for example Burnett et al., "Absolute refractive indices and thermal coefficients of $CaF_2$, $SrF_2$, $BaF_2$, and LiF near 157 nm", *Appl. Opt.* 41, 2508–2513 (2002) and French et al., "Immersion Fluid Refractive Indices Using Prism Minimum Deviation Techniques", Optical Microlithography XVII, SPIE 5377–173, (2004).

A liquid-filled prism cell was used. The cell was a 60° equilateral, stainless steel, liquid prism, which included two 12.7 mm diameter×2 mm thick $CaF_2$ windows with Viton® polymer o-ring seals, Luer-Lok® fittings for loading samples. The cell was disassembled for cleaning.

Prior to each use the cell was flushed with Vertrel® XF, through both Luer-Lok® fittings using a 1 ml BD glass syringe to flush out the previous specimen. Then the prism cell was dried with air from an air puffer bulb. The cell was then disassembled for cleaning. The $CaF_2$ windows and the stainless steel cell body were cleaned by ultrasonic agitation in closed vials containing Vertrel® XF for 30–60 seconds The $CaF_2$ windows were rubbed with a cotton swab wet with Vertrel® XF after removal from the ultrasonic bath. then dried with air from a puffer bulb. The cell body was removed from the cleaning bottle then dried with air from a puffer bulb. The cell was then reassembled.

Loading the Prism Cell in Nitrogen (Nitrogen Dry Box)

A cleaned, assembled cell, Teflon® TFE plugs, a clean 1 ml BD syringe and a sealed bottle of the selected sample material were placed into either the Series 100 Plexiglas glove box or the Nexus model 100043 dry box as described herein above.

The sample bottle was then opened and approximately 1 ml of the sample was transferred from it, (this fluid had been filtered through a 0.20 micron PTFE filter), following the method previously described herein above to minimize bubble formation.

When the sample was stored with an adsorbent, the liquid was poured into a clean 15 ml BD syringe with a 0.2 micrometer PTFE Luer-Lok® filter. Using the syringe, the liquid was transferred through the filter into a clean, dry 20 ml vial. Approximately 1 ml of the thus filtered sample was transferred into the cell as described above.

Minimum Deviation Index Method

The equilateral liquid prism was mounted on the VASE® which was equipped with a computer controlled, stepper motor driven $\ominus$-2$\ominus$ angle-of-incidence stage. The sample rotation stage and the detector arm rotation stage were controlled separately during the measurement. For a given wavelength and incident angle, the detector arm was swept through a range of angles to determine the transmission angle. This process was repeated for a range of incident angles. Once the minimum deviation angle was determined, the index was determined according to the method of Sinnock et al., *op. cit.*

The VUV-VASE ellipsometer was used for index measurements at a nominal temperature of 32° C. The DUV-VASE ellipsometer was used for index measurements at a nominal temperature of 22° C.

The work described herein below was performed in glove bags, glove boxes and dry boxes. The glove bag was a polyolefin bag with glove shaped appendages provided for manipulation and a crude seal at the bottom made by folding. The glove box was a homemade box fabricated by gluing together sheets of PMMA boxes, and fitting out the box with regular dry box gloves. The dry box was a commercial box with high quality seals and ports. Applying Henry's law for oxygen concentrations as high as 100 ppm in nitrogen still results in only parts per billion-dissolved oxygen. There is no experimental evidence that the specific enclosure employed made a difference in results.

Example 1

In this example, decahydro-2-trifluoromethyl-2,3,3-trifluoro-1,4:5,8-dimethanonaphthalene is prepared at low absorbance without the use of the sulfuric acid wash A 400 ml autoclave was charged with fresh distilled cyclopentadiene (110 g) and hexafluoropropylene (120 g, DuPont). The mixture was heated at 200° C. for 48 hours. The reaction mixtures from three identical reactions were combined and distilled at reduced pressure to give 5-trifluoromethyl-5,6,6-trifluorobicyclo[2,2,1]hept-2-ene (160.5 g, bp<47° C./0.4 Torr, yield 31%) and octahydro-6-trifluoromethyl-6,7,7-trifluoro-1,4:5,8-dimethanonaphthalene (268.6 g, bp 65–81° C./0.3 Torr, yield 40%).

A 400 ml autoclave was charged with octahydro-6-trifluoromethyl-6,7,7-trifluoro-1,4:5,8-dimethanonaphthalene (177 g, prepared as described above), methanol (100 ml, Burdick & Jackson, HPLC grade), and palladium on activated carbon (1 g containing 10% Pd, Alfa products, powder). The autoclave was closed and sealed, then shaken under 50 psig hydrogen pressure for 1 hour at room temperature. The hydrogen pressure was gradually increased to 200 psig over next hour at room temperature followed by 600 psig at 150° C. for 2 hour. After being cooled to room temperature, the reaction mixtures from two identical runs were combined and filtered to remove the catalyst. The filtrate was mixed with water (200 ml). The organic layer was isolated, diluted with methylene chloride (250 ml) and washed with water (100 ml), dried over $Na_2SO_4$ (EM Science, anhydrous granular). After removal of $Na_2SO4$, the solution was distilled to remove the solvent and further distilled at reduced pressure Decahydro-2-trifluoromethyl-2,3,3-trifluoro-1,4:5,8-dimethanonaphthalene (269 g, bp 114–117° C./2 Torr, yield 75%). The fluid was transferred to a clean bottle (VWR, VWR® TraceClean™ bottle with Teflon® TFE lined closure) and purged with nitrogen. The bottle was added activated silica gel (about ⅓ in volume of the fluid) in a dry box. The bottle was closed and shaken for about 30 seconds, then allowed to sit at room temperature for a few days. The fluid was decanted into another clean bottle and added activated silica gel (about ⅓ in volume of the fluid) in a dry box. Silica gel (Aldrich catalog number 24,982–3, type 3, 8 mesh) was dried at 500° C. for two hours before using. After a total three such silica gel treatments, the fluid was filtered through an Acrodisc® CR 25 mm syringe filter with 200 nm PTFE membrane (Pall Life Science). Its transparency was measured by the relative transmission method with 0.145, 0.4 and 0.6 cm path length

Example 2

In this example, decahydro-2-trifluoromethyl-1,4:5,8-dimethanonaphthalene is prepared incorporating the sulfuric acid wash step A 400 ml autoclave was charged with octahydro-6-trifluoromethyl-1,4:5,8-dimethanonaphthalene (125 g, prepared as described in Example 1), methanol (100 ml, Burdick & Jackson, HPLC grade), and palladium on activated carbon (1 g containing 10% Pd, Alfa products, powder). The autoclave was closed and sealed, then shaken under 50 psig hydrogen pressure for 1 hour at room temperature. The hydrogen pressure was gradually increased to 200 psig over next hour at room temperature followed by 600 psig at 150° C. for 2 hour. After being cooled to room temperature, the reaction mixture was filtered to remove the catalyst. The filtrate was divided into two layers. The bottom layer was isolated and washed with water (2×50 ml), dried over Na2SO4 (EM Science, anhydrous granular). After removal of Na2SO4, the liquid was distilled to give decahydro-2-trifluoromethyl-1,4:5,8-dimethanonaphthalene (92.3 g, bp 59–60° C./0.15 Torr, yield 73%). Further purification: About 40 g of decahydro-2-trifluoromethyl-1,4:5,8-dimethanonaphthalene was mixed with conc. sulfuric acid (5 ml). The resulting mixture was stirred at room temperature for 24 hours. The top layer was isolated and washed with NaHCO$_3$ (0.5M), water, dried over Na$_2$SO$_4$. After removal of Na$_2$SO$_4$, the liquid was distilled to give a fluid. The fluid was transferred to a clean bottle (VWR, VWR® TraceClean™ bottle with Teflon-lined closure) and purged with nitrogen. The bottle was added activated silica gel as provided in Example 1 (about ⅓ in volume of the fluid) in a dry box. The bottle was closed and shaken for about 30 seconds, then allowed to sit at room temperature for a few days. The fluid was filtered through an Acrodisc® CR 25 mm syringe filter with 200 nm PTFE membrane (Pall Life Science). The filtered fluid had an absorbance 2.0 cm$^{-1}$ at 193 nm when measured by the cuvette method with a 0.1 cm path length. It had a refractive index 1.60 at 193 nm at the measurement temperature of 22° C.

Comparative Example 1

In this comparative example, the decahydro-2-trifluoromethyl-1,4:5,8-dimethanonaphthalene of Example 2 is purified only by using absorbents, the sulfuric acid being omitted.

Decahydro-2-trifluoromethyl-1,4:5,8-dimethanonaphthalene (42 g, as described in Example 2) was transferred to a clean bottle (VWR, VWR® TraceClean™ bottle with Teflon-lined closure) and purged with nitrogen. In a dry box, activated molecular sieves were added to the bottle (about ⅓ in volume of the fluid) in a dry box. The bottle was closed and shaken for about 30 seconds, then allowed to sit at room temperature for a few days. This liquid in the bottle was transferred to another clean bottle (same as described above) and combined with alumina (about ⅓ in volume of the liquid) in a dry box. The bottle was closed and shaken for about 30 seconds, then allowed to sit at room temperature for a few days. This liquid was transferred to another clean bottle as above, and combined with silica gel (about ⅓ in volume of the liquid) in a dry box. The bottle was closed and shaken for about 30 seconds, then allowed to sit at room temperature for a few days. The liquid was filtered through an Acrodisc® CR 25 mm syringe filter with 200 nm PTFE membrane (Pall Life Science). The filtered fluid had an absorbance 39 cm$^{-1}$ at 193 nm when measured by the cuvette method with a 0.1 mm path length.

Molecular sieves (3A, 8–12 mesh, Aldrich #20858-2) were activated for two hours under vacuum at 500° C.

Aluminum oxide (granular, 4–8 mesh, Aldrich #30911-7) were activated for two hours under vacuum at 500° C.

What is claimed is:

1. A process comprising
  combining in a pressure vessel an olefin represented by the Structure I

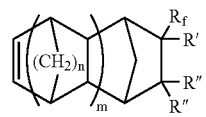

wherein $R_f$ is a fluorinated alkyl of 1–10 carbons that is linear, branched, or cyclic; R' is H, F, an alkyl of 1–6 carbons that is linear, branched, or cyclic, or a fluorinated alkyl of 1–6 carbons that is linear, branched, or cyclic;
  each R" is independently H or F, n=0 or 1, and m=1 or 2 provided that m is not 2 when n=0; and a hydrogenation catalyst;
  sealing the vessel;
  removing water vapor and air;
  pressurizing the vessel with hydrogen to a pressure in the range of 10 to 1000 psig;
  heating the vessel to a temperature from room temperature to 200° C.;
  allowing the resulting reaction to proceed for 1 to 8 hours to form a reaction product;
  contacting said reaction product with sulfuric acid or oleum to form an acid treated reaction product; and,
  contacting said acid treated reaction product with silica gel.

2. The process of claim 1 wherein n=1 and m=1.

3. The process of claim 1 wherein R' is H or F.

4. The process of claim 1 wherein $R_f$ is perfluoromethyl or perfluoroethyl.

5. The process of claim 1 wherein $R_f$ is perfluoromethyl.

6. The process of claim 1 wherein the F/H ratio is 0.5 or lower.

7. The process of claim 1 further comprising a concentration of oxygen below 1 ppm.

8. The process of claim 1 wherein R' is H or F, each R" is H or F, n=1, m=1, and $R_f$ is perfluoromethyl.

9. The process of claim 1 wherein the pressure of hydrogen is gradually raised from 10 psig to 1000 psig.

10. The process of claim 9 wherein the pressure of hydrogen is gradually raised from 10 psig to 600 psig.

11. The process of claim 1 wherein the temperature of the reaction mixture is raised from room temperature to 150° C.

12. The process of claim 1 wherein the catalyst is selected from palladium on carbon, Raney nickel, Raney cobalt, platinum metal, platinum oxide, rhodium, ruthenium and zinc oxide.

13. The process of claim 12 wherein the catalyst is palladium on carbon.

* * * * *